United States Patent [19]
Buckminster et al.

[11] Patent Number: 5,265,642
[45] Date of Patent: Nov. 30, 1993

[54] PRESSURE RELIEF VALVE IN A CAP

[75] Inventors: William F. Buckminster, Voorhees; Richard J. Viscusi, Laurel Springs, both of N.J.; Larry V. Greenley, Vienna, Va.

[73] Assignee: SP Industries Limited Partnership, Miami, Fla.

[21] Appl. No.: 910,247

[22] Filed: Jul. 9, 1992

Related U.S. Application Data

[63] Continuation-in-part of Ser. No. 750,060, Aug. 27, 1991, abandoned.

[51] Int. Cl.$^5$ .................. F16K 17/04; B01D 53/00
[52] U.S. Cl. .................. 137/469; 137/538; 137/540; 210/198.2
[58] Field of Search .................. 137/469, 538, 540; 55/386; 210/198.2

[56] References Cited

U.S. PATENT DOCUMENTS

| | | | |
|---|---|---|---|
| 1,879,020 | 9/1932 | Balsiger | 137/538 |
| 2,305,519 | 12/1942 | Dunmire | 137/538 |
| 2,364,812 | 12/1944 | Pierson | 137/469 |
| 2,888,946 | 6/1959 | Barron | 137/469 |
| 3,025,869 | 3/1962 | Kenfield | 137/469 X |
| 3,194,260 | 7/1965 | Price | 137/469 |
| 3,373,764 | 3/1968 | Munn | 137/469 |
| 3,922,223 | 11/1975 | Burkhartsmeier | 55/386 X |
| 4,121,619 | 10/1978 | Pauliukonis | 137/469 |
| 4,142,549 | 3/1979 | Autry | 137/469 |
| 4,448,684 | 5/1984 | Paradis | 55/386 X |
| 4,504,081 | 3/1985 | Shimizu et al. | 137/469 X |
| 4,541,452 | 9/1985 | Paradis | 55/386 X |
| 4,994,180 | 2/1991 | Sims et al. | 55/386 |

OTHER PUBLICATIONS

Chromware HPLC Mobile Phase Handling Systems, Nov. 3, 1991.

*Primary Examiner*—John Rivell
*Attorney, Agent, or Firm*—Arnold, White & Durkee

[57] ABSTRACT

A pressure relief valve in a cap, and more particularly a pressure relief valve in a cap for use with pressure vessels in chromatography systems. In one exemplary application the valve is contained within the cap of a pressure chromatography column. In a second exemplary application the valve is contained within the cap of a mobile phase reservoir of a high performance liquid chromatography system. The valve generally comprises a body, a sealing element, and a force applying means. The body of the valve is formed into the cap and defines an inlet in communication with the interior of the column, an outlet in communication with ambient air, a first bore, and a seat. The sealing element slides within the body and is urged into sealing contact with the seat by the force applying means. The sealing element has a raised lip at its sealing face to provide a substantial sealing force per unit of sealing surface area.

3 Claims, 2 Drawing Sheets

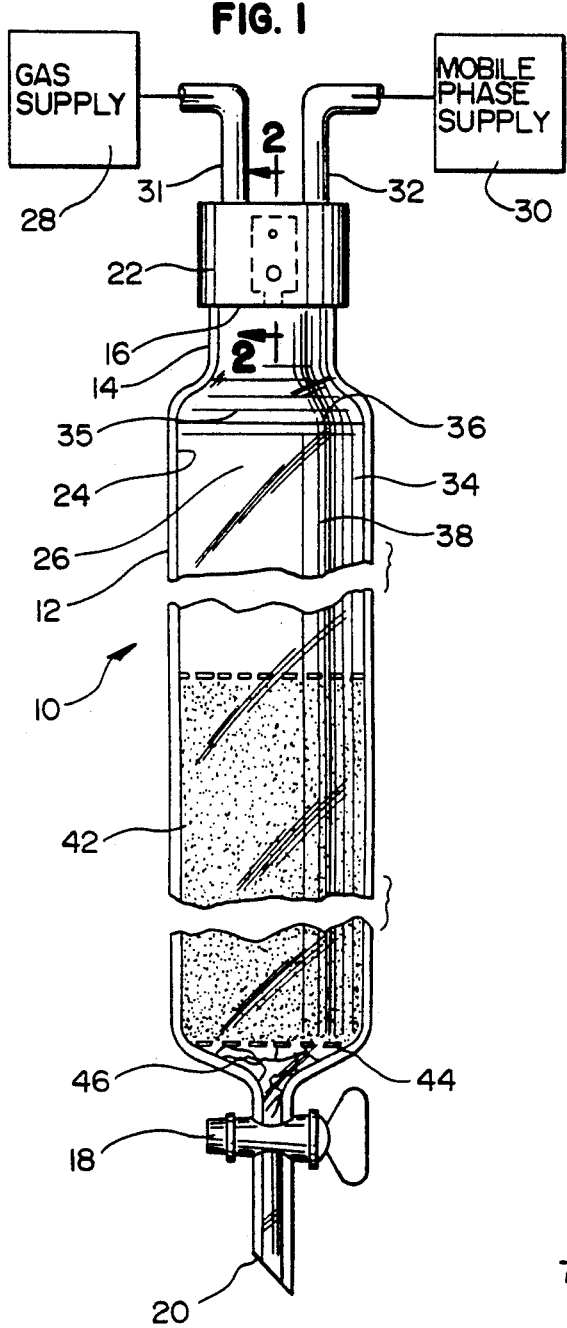
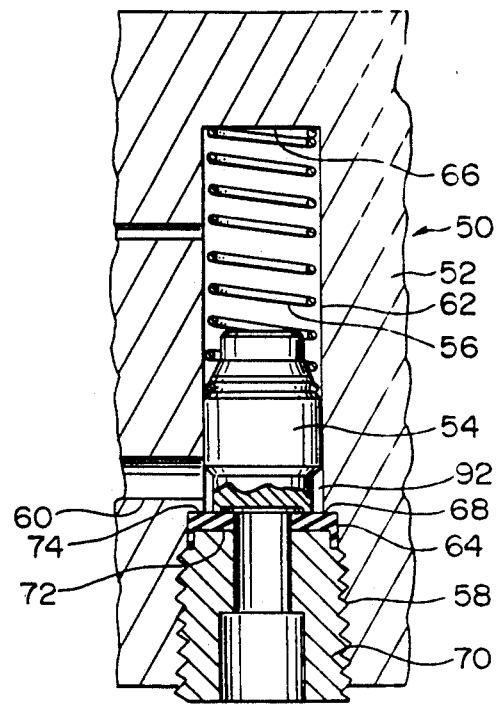
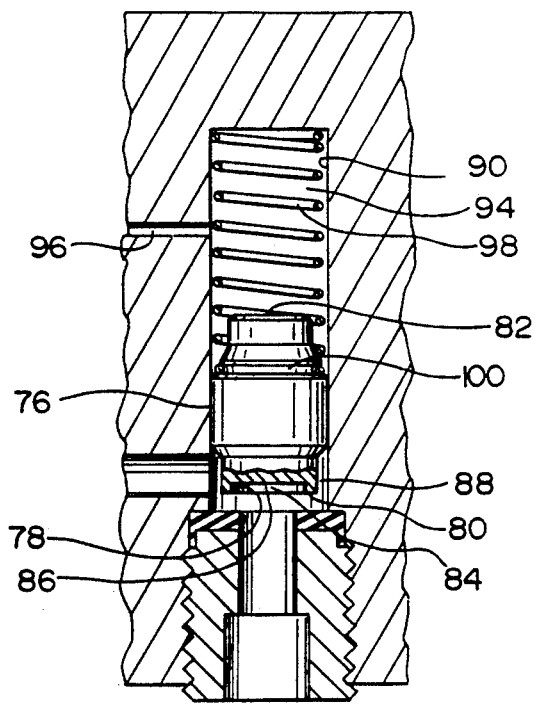

PRESSURE RELIEF VALVE IN A CAP

This is a continuation-in-part of application Ser. No. 07/750,060, filed Aug. 27, 1991, now abandoned entitled "Pressure Relief Valve" and which is assigned to the same assignee as the present invention.

FIELD OF THE INVENTION

The present invention relates to a pressure relief valve in a stopper or cap for a pressure vessel, and more particularly a pressure relief valve in a stopper or cap for a mobile phase reservoir used in a high performance liquid chromatography system.

BACKGROUND OF THE INVENTION

Chromatography is the separation of mixtures of chemical substances into their component parts by chromatographic adsorption for analytical purposes. Chromatographic adsorption is the preferential adsorption or differential retention of chemical compounds on the basis of molecular size, charge, hydrophobicity, or biospecific affinity by an adsorbent material. Liquid chromatography is a form of chromatography which employs a liquid as the "mobile phase" and a solid, or a liquid on a solid support, as the stationary adsorbent phase. A liquid chromatography system typically includes the following elements connected together in a manner well known to those of ordinary skill in the field: a column, a pump, an injector, a reservoir, a detector, and a recorder.

In column chromatography, the liquid mobile phase is introduced into the top of a cylindrical column and forced through a bed of material to separate the liquid into various components. Solvents and chemical reagents are used to facilitate the separation. Therefore, the chromatography column, associated valves, and any other related apparatus should be made of materials which will not react with solvents or chemical reagents. For biological separations, sterilizable materials may be necessary. Glass is frequently chosen as the material for the column because it is resistant to common solvents, reagents, sterilizing agents and heat, and its transparency permits an analyst to watch the separation as it takes place.

Pressure chromatography employs a positive pressure within the head of the column, usually about three psi (about 2 $N/cm^2$), to force the mobile phase through the bed of material. The pressure head above the liquid has commonly been controlled by a pressure regulator valve outside the column. However, the pressure which glassware can withstand is minimal. If the pressure within the column significantly exceeds the normal operating pressure, a glass column may shatter, thus ruining the separation and creating a hazard. Despite this problem, pressure relief valves have not been used in pressure chromatography columns.

At the top of a pressure chromatography column is a mouth, through which the bed is introduced. Before or after the mobile phase is introduced, the mouth is capped so a pressure above ambient pressure can be maintained within the column. Positive pressure is maintained by supplying a low-pressure inert gas, such as helium, to the column through its cap. A reservoir may also be connected to the head of the column to increase the amount of mobile phase which may be contained in the column. In that case, the reservoir has a mouth which is capped, and an inert gas is introduced to the reservoir to pressurize the reservoir and the column.

The mouth of the column or reservoir, and thus its cap, frequently has a smaller diameter. The cap must have two, three or even four independent apertures for admitting inert gas, the mobile phase containing the sample to be analyzed, a fresh elution solvent, a thermometer, or other materials or apparatus without releasing the pressure within the column. Consequently, the cap has little space in which additional apparatus can be mounted.

In another refinement of general liquid chromatography, specific modifications in the design and nature of the column, the stationary adsorbent phase contained in the column, the injector, and the chromatographic conditions (e.g., pressure, temperature, flow rate, solvent properties) are made in order to provide improved separation and resolution for more refined analysis of particular samples. This refinement of liquid chromatography, well understood by those of ordinary skill in the field, is termed high performance liquid chromatography ("HPLC"), and has achieved widespread application in the analysis of a multitude of biological and chemical samples.

The typical mobile phase reservoir in an HPLC system is a glass container which may have been designed specifically for use in such a system. In a manner similar to that described above with regard to pressure chromatography, pressure is used in HPLC reservoirs for two reasons: (i) to keep atmospheric gases away from the liquid mobile phase contained in the reservoir; and (ii) to supply the mobile phase to the system's pump at a slight positive pressure, thus improving the performance of the pump's check valves. Furthermore, an HPLC reservoir can be accidentally pressurized during the widely used technique of helium sparging. This technique consists of bubbling helium gas through the mobile phase contained in a glass reservoir. If no outlet vent for the helium is provided, the glass reservoir will become pressurized, and could explode.

As discussed above in relation to pressure chromatography, the mouth of the mobile phase reservoir typically has a relatively small diameter, and therefore a cap for the reservoir has a small diameter as well. Moreover, and again as discussed in relation to pressure chromatography, the cap should contain at least the following independent apertures: an aperture for helium sparging; for egress of the mobile phase from the reservoir; and for egress of the helium used for sparging. The cap may also contain simple, manually opened and closed "on/off" valves for controlling sparging; for mobile phase egress to the pump, and for venting or sealing during sparging or blanketing, respectively. The cap may also possess filtration capabilities. Therefore, space considerations may be even more critical in a cap for a mobile phase reservoir in an HPLC system than in a pressure chromatography system.

Valves are commonly used in pressure vessels to control the flow and pressure of fluids. Most common valves include a body or housing, a seat, a disk or sealing element, and means for urging the sealing element into sealing engagement with the seat to restrict flow or maintain pressure into or out of the vessel.

The inventors have found that Kalrez fluorocarbon material ("Kalrez" is a trademark of E.I. du Pont de Nemours & Co., Wilmington, Del.) is useful as a seat material in a valve for pressure chromatography. However, Kalrez is not readily available in durometers of less than 75 Shore A. Such a high durometer seat material requires that the sealing element of a valve be urged into the seat with a substantial seating force (expressed as pounds per square inch or newtons per square centimeter of valve disk to seat contact area) to deform the seat material and create a positive seal. F In valves which may have a large cross-section, or which maintain a relatively large pressure differential, the area of the seat contacted by the valve disk may not be critical. In a large valve, the effective piston area of the sealing element can be large enough that a small head of pressure controlled by the valve can counteract a significant seating force and force the valve open. (The "effective piston area" of a valve disk is defined here as the area of the seated valve element normal to its direction of unseating upon which the pressure at the valve inlet acts and thus urges the element toward an unseated position.) In high pressure applications, the substantial pressure acting on even a small effective piston area of the sealing element can be sufficient to counteract a significant seating force.

It is difficult to design a low pressure differential, small cross-section pressure relief valve which exerts a high enough seating force per square unit of cross-sectional area of the sealing surface to deform the seat while having a substantial enough effective piston area to develop a force sufficient to counteract the seating force when pressure relief is desired.

Yet another problem in pressure relief valve design is how to design a valve which has a few parts and is easily assembled and disassembled for repair or cleaning.

In addition, and particularly in HPLC systems, loose fitting HPLC mobile phase reservoir caps are unable to maintain positive pressure in the mobile phase reservoir. Caps unable to maintain positive reservoir pressure require continuous helium sparging to maintain the mobile phase in a degassed state. Continuous sparging wastes helium and can lead to venting of environmentally undesirable organic solvents. Caps unable to maintain positive reservoir pressure can also cause the check valves in the HPLC system's pump to operate in an unreliable manner. However, caps which provide a tight fit are unable to avoid over-pressurization within the glass reservoir and can create a hazardous situation in the laboratory.

SUMMARY OF THE INVENTION

The present invention addresses the above problems by employing in a cap or stopper a pressure relief valve comprising a valve body, a sealing element, and a force applying means to bias the sealing element into contact with the seat. The valve is adapted to open when the pressure within a closed vessel exceeds a desired value.

The valve body has an inlet, an outlet downstream of the inlet, a seat interposed between the inlet and outlet, and a first bore extending downstream of the seat.

The sealing element is disposed downstream of the seat. The sealing element has an outer wall slidingly received in the first bore. A raised lip of the sealing element defining an annular sealing surface encloses a recess of the sealing element which defines a piston surface. The sealing element is movable within the first bore to seat or unseat its raised lip on the seat.

The raised lip of the sealing element has a smaller outer diameter than the outer wall of the sealing element. An annular space is thus defined between the first bore and the raised lip. At pressures in the pressure vessel which are below the predetermined relief pressure, the annular sealing surface of the raised lip is biased into sealing contact with the seat by the force applying means.

The valve overcomes the problem of low sealing pressure against the seat because the sealing surface of the raised annular lip has an area significantly less than the effective piston area of the sealing element. The small area of the sealing surface allows a small force exerted by the force applying means on the sealing element to apply a relatively high sealing force per unit area of the sealing surface. Thus, a small force applied to the sealing element results in a large sealing force to adequately deform the seat and create a sufficient seal. The effective piston area for generating the necessary unseating force is small, so the valve has a small cross-section. Nonetheless, the ratio of the effective piston area to the sealing area is large. Hence a relatively small pressure change within the pressure vessel is required to unseat the sealing element.

In a preferred embodiment of the present invention, the pressure relief valve is included in a stopper or cap for a pressure chromatography apparatus. In an alternative preferred embodiment of the present invention the pressure relief valve is included in a cap for a mobile phase reservoir in a HPLC system. The small cross-section of the valve allows it to be built into such stoppers or caps for sealing the opening of such "pressure vessels" (this term intended to include, for example, a pressure chromatography column or reservoir and a mobile phase reservoir for HPLC), while allowing sufficient room for at least four other ports and/or valves in a cap with standard ¼"-28 threads. Moreover, the pressure relief valve, although small, opens at relatively low pressures, discriminates between two relatively low pressures (for example, it can seal at 3 psi and open at 10 psi), continues to open at a preset pressure even after the seat has been irreversibly compressed by steady valve spring pressure, and contains a gas within the pressure vessel without significant loss through the valve. Such a cap with an integrated pressure relief valve allows for tight sealing of pressure vessels and maintenance of positive pressure within the vessel, without the potential for dangerous pressure build-up and the consequent explosion of glassware.

The valve can be easily assembled and disassembled, and can have five or fewer separate components. The valve is made of relatively inert materials which are resistant to heat and to reactions with chemical reagents and solvents, so it can be repeatedly cleaned and sterilized.

BRIEF DESCRIPTION OF THE DRAWINGS

FIG. 1 is a schematic front elevational view of a pressure chromatography apparatus including a pressure relief valve in a cap according to the present invention. The valve in the cap is shown in phantom.

FIG. 2 is a sectional view of the valve taken along line 2—2 of FIG. 1 and FIG. 5 with the sealing element in its normal (sealed) position.

FIG. 3 is similar to FIG. 2 except that the sealing element is in its relief (open) position.

Figure 4:
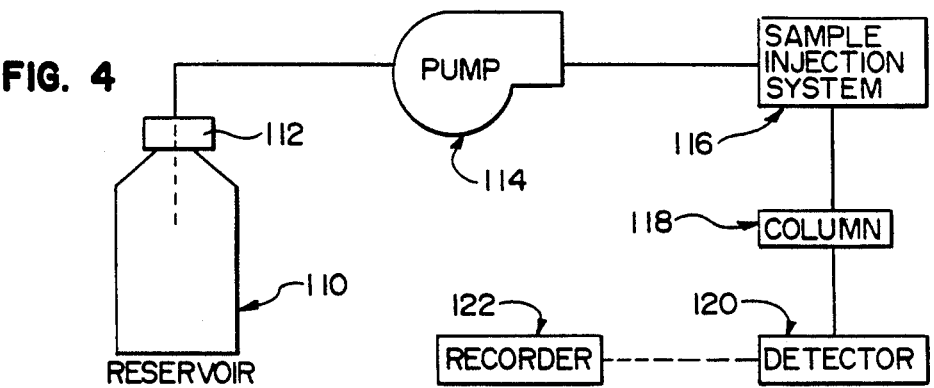
FIG. 4 is a schematic diagram of a generalized HPLC system.

The drawings are not necessarily to exact scale and certain features are illustrated schematically. Physical relationships of components expressed by terms such as "upstream", "downstream" or the like have reference solely to the orientation depicted in the drawings relative to flow into the body of the valve through the inlet and out of the body through the outlet. Actual embodiments or installations thereof may differ.

While some mechanical details of the illustrated embodiments of the invention have been omitted or shown schematically, such details are not necessary to explain the present invention and are considered well within the comprehension of those skilled in the art in light of the present disclosure. It should also be understood that the invention is not limited to the particular embodiments illustrated. The scope of the invention is indicated by the claims.

DESCRIPTION OF THE PREFERRED EMBODIMENTS

Reference is made herein to FIGS. 1-5 of the drawings, wherein like reference characters refer to like elements in each view.

FIG. 1 illustrates a pressure chromatography apparatus including a pressure relief valve in the cap according to the present invention. The pressure chromatography apparatus 10 includes a column 12 having a mouth 14 with an opening 16, an exit valve 18 and an exit port 20. The column 12 is sealed at the opening 16 by a cap 22. The cap 22 and interior wall 24 of the column 12 define a column chamber 26. A gas supply 28 and a mobile phase supply 30 are provided. The gas supply 28 and mobile phase supply 30 communicate with the column chamber 26 through suitable conduits 31, 32 inserted through corresponding apertures (not illustrated) through the cap 22.

The top of the column 12 is a reservoir 34 for the mobile phase. In an alternative embodiment, the reservoir 34 may be enlarged, and may also be a separate vessel having an inlet which is capped by the cap 22, and having an outlet which is in communication with the column chamber 26.

During pressure chromatography, a headspace 35 is present above the surface 36 of the fluid 38 in the reservoir 34. This headspace 35 is maintained next to the cap 22 so the fluid in contact with the cap 22 is a gas, preferably an inert gas, instead of a liquid. The headspace 35 can be maintained at an elevated pressure by providing an inert gas (such as helium) from the gas supply 28. Therefore, the fluid in the reservoir 34 and column chamber 26 is maintained at an elevated pressure to force the fluid 38 through an active bed of material 42 which is retained on a support bed 44 of a coarser support material 46. The support material 46 prevents the bed 42 from passing through the exit valve 18 and out the exit port 20.

A more detailed description of pressure chromatography is presented in U.S. Pat. No. 4,293,422, which is hereby incorporated by reference herein for its description of that process.

A pressure relief valve 50 is provided to normally seal reservoir 34 of the column chamber 26 from ambient pressure outside the column chamber 26. The pressure relief valve 50 will open to relieve pressure within the column chamber 26 if the chamber pressure exceeds the relief pressure designed into the valve 50.

Referring to FIGS. 1, 2 and 3, the pressure relief valve 50 generally comprises a body 52, a sealing element 54, and a force applying means 56.

The body 52 is formed into the cap 22, which is made of glass-powder-filled Teflon material in this embodiment. ("Teflon" is a trademark of E.I. du Pont de Nemours & Co. for polytetrafluoroethylene). The body defines an inlet 58 in communication with the column chamber 26, an outlet 60 in communication with ambient air, a first bore 62, and a seat 64. The first bore 62 terminates at an end wall 66. The seat 64 is formed as a separate part from the remainder of the body 52, and is retained against the shoulder 68 by a seat retainer 70 threaded into the inlet 58. In this embodiment the seat 64 is formed of Kalrez fluoropolymer rubber material having durometer value of about 75 (Shore A). Alternatively, the seat could be an integral part of the body 52. The seat 64 has an upstream side 72 and a downstream side 74.

The sealing element 54 has an outer wall 76 slidingly received within the first bore 62, a raised lip 78 with an annular sealing surface 80, and a rear face 82 opposed to the raised lip 78. The annular sealing surface 80 has a surface area of about 1/100 square inch (about 7 mm$^2$) in this embodiment. The lip 78 encloses a recess 84 defining a piston surface 86. In this embodiment the effective piston area enclosed by the lip 78 is about 1/40 square inch (about 16 mm$^2$). Thus, the piston area is greater than (in fact, more than twice as great) the sealing surface area of the valve. The raised lip 78 has an outer surface 88. The outer wall 90 of the first bore 62, the outer surface 88 of the raised lip 78 and the downstream side 74 of the seat 64 define an annular space 92 in communication with the outlet 60. The rear face 82 of the sealing element 54, the first bore 62 and the end wall 66 of the first bore 62 define a chamber 94. The chamber 94 is vented to ambient pressure by a bore 96, so the air within the chamber 94 does not substantially affect the travel of the sealing element 54 within the first bore 62.

One force applying means in the illustrated embodiment is a compression spring 98 disposed within the chamber 94. In this embodiment, the spring is made of 316 stainless steel. The spring 98 acts between the end wall 66 of the first bore 62 and the rear face 82 of the sealing element 54 to urge the annular sealing surface 80 into sealing contact with the downstream side 74 of the seat 64. As shown, the rear face 82 of the sealing element 54 may have a groove 100 to attach the spring 98 to the sealing element 54 for ease of assembly.

In this embodiment, the spring applies a closing force of about 3 pounds (about 13 Newtons) per square inch (about 6 cm$^2$) of the effective piston area of the sealing element 54. The weight of the sealing element 54 is another force applying means in this embodiment, because the first bore 62 is vertically oriented with the seat 64 at the bottom and the sealing element 54 is fairly heavy, being fabricated from 316 stainless steel in this embodiment.

Many other equivalent force applying means can readily be devised within the scope of the present invention. For one example, gas under pressure could be introduced through the bore 96 into the chamber 94 to define a gas spring. For another example, at least part of the sealing element 54 could be deformable and bear directly against the end wall 66.

When the pressure in the headspace 35 is at or below the intended pressure, such as about 10 psi (about 7 N/cm$^2$) in this embodiment, the force applying means overcomes the tendency of this operating pressure to unseat the annular sealing surface 80 from the seat 64. The sealing surface 80 is urged into contact with the downstream side 74 of the seat 64 with sufficient force to seal the seat 64 and thus retain the pressure within the pressure chromatography apparatus 10. In this embodiment, a suitable sealing force applied to the annular sealing surface 80 is about 50 psi (about 34 N/cm$^2$).

When the force generated by the gas supply 28 in the headspace 35 acting against the piston surface 86 becomes great enough to overcome the counteracting seating force applied by the force applying means 56 acting on the sealing element 54, the sealing element 54 moves away from the downstream side 74 of the seat 64. In this unseated condition, the pressure in the headspace 35 communicates with the outlet 60 through the annular space 92, thus relieving the excess pressure. In this embodiment, the valve is designed to being releasing pressure at about 8 psi (about 5.5 N/cm$^2$) within the headspace 35 and to fully release at about 12 psi (about 8 N/cm$^2$) within the headspace 35.

In this embodiment, the diameter of the first bore 62 is about ¼ inch about 6 mm), so the valve is readily built into a cap 22, notwithstanding the apertures through the cap 22 for introducing the mobile phase and pressurizing gas.

FIG. 4 shows a schematic illustrations of a generalized HPLC system. The mobile phase reservoir 110 with a pressure relief valve in a cap of the present invention 112 is connected to a pump 114 which draws the mobile phase from the reservoir 110 into the HPLC system. The pump 114 then pumps the mobile phase to the injector 116 which injects the mobile phase and the sample into the column 118. The mobile phase then moves into the detector 120 and a recorder 122 analyzes the signal from the detector 120.

Figure 5:
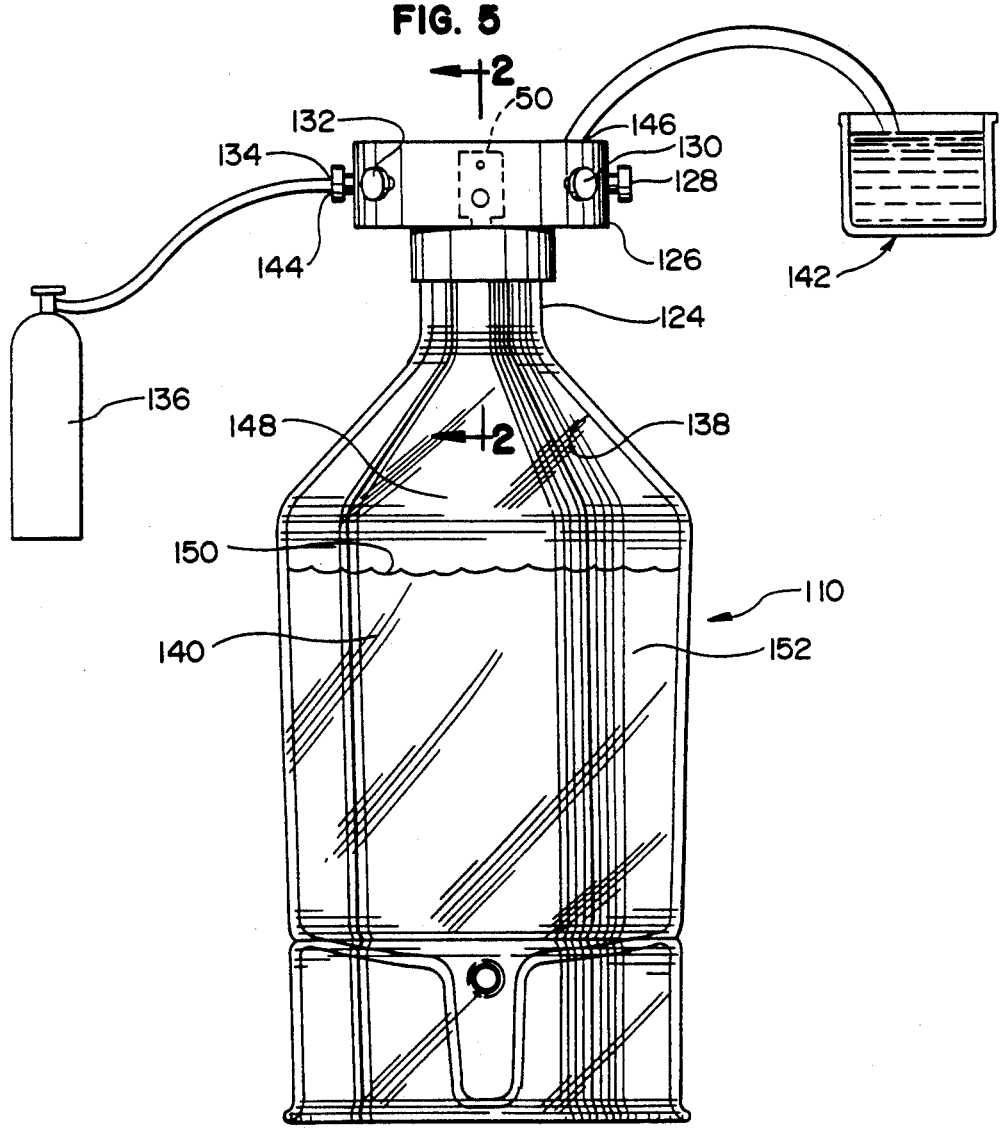
FIG. 5 is an elevational view of a mobile phase reservoir for an HPLC system including a pressure relief valve in a cap according to the present invention. The valve in the cap is shown in phantom.

FIG. 5 illustrates a mobile phase reservoir for an HPLC system including a pressure relief valve in a cap according to the present invention. The mouth 124 of the mobile phase reservoir 110 is capped by a cap 126 allowing for, at a minimum, egress of the mobile phase to the pump 114 as shown in FIG. 4. In this example, as shown in FIG. 5, the cap 126 includes a pump valve 128, a filter valve 130, a vacuum/vent valve 132 and a sparge valve 134 connected to a gas supply 136, along with the pressure relief valve 50. The cap 126 and the interior wall 138 of the mobile phase reservoir 110 define a chamber 140. The gas supply 136 and an HPLC pump 142 communicate with the chamber 140 through suitable conduits 144 and 146 (respectively) inserted through corresponding apertures (not illustrated) through the cap 126.

During HPLC, a headspace 148 is present above the surface 150 of the fluid 152 in the mobile phase reservoir 110. This headspace 148 is maintained next to the cap 126 so that the substance in contact with the cap 126 is a gas, preferably an inert gas, rather than a liquid. The headspace 148 can be maintained at an elevated pressure by providing an inert gas (such as helium) from a gas supply 136 via the sparge valve 134. Thus, according to the present invention, a pressure relief valve 50 in a cap 126 is attached to seal the mobile phase reservoir 110 from ambient pressure outside the reservoir, as well as to maintain a slight positive pressure within the headspace 148 of the reservoir. The pressure relief valve 50 will open to relieve pressure within the headspace 148 of the mobile phase reservoir 110 if the pressure within the headspace 148 exceeds the relief pressure designed into the valve 50.

The performance of the pressure relief valve 50 in a cap 126 for a mobile phase reservoir 110 in an HPLC system is intended to be substantially identical to that in the embodiment described in detail above. The differences with regard to the valve's function in this embodiment are specific to its function in a cap for an HPLC system's mobile phase reservoir. Specifically, referring to FIGS. 2, 3 and 5, when the pressure in the headspace 148 of the mobile phase reservoir 110 is at or below the intended pressure, for example about 10 psi, the force applying means overcomes the tendency of this operating pressure to unseat the annular sealing surface 80 from the seat 64, as illustrated in FIGS. 2 and 3. The sealing surface 80 is urged into contact with the downstream side 74 of the seat 64 with sufficient force to seal the seat 64 and thus retain the pressure within the headspace 148. In this embodiment, a suitable sealing force applied to the annular sealing surface 80 is about 50 psi (about 34 N/cm$^2$).

When the pressure generated in the headspace 148 of the mobile phase reservoir 110 by sparging gas entering through a sparge valve 134 in the cap 126, or by blanketing gas entering through the vacuum vent valve 132, or by liquid mobile phase backing up into the reservoir through the pump valve 128 acts against the piston surface 86 with sufficient force to overcome the counteracting seating force applied by the force applying means 56 acting on the sealing element 54, the sealing element 54 moves away from the downstream side 74 of the seat 64. In this unseated condition, the pressure in the headspace 148 communicates with the outlet 60 through the annular space 92, thus relieving the excess pressure. In this embodiment, the valve is designed to begin releasing pressure at about 8 psi (about 5.5 N/cm$^2$) within the headspace 148 and to fully release at about 12 psi (about 8 N/cm$^2$) within the headspace 148.

In this embodiment, as in that exemplified above, the diameter of the first bore 62 is about ¼ inch (about 6 mm), so the valve is readily incorporated into a cap 126, notwithstanding the apertures through the cap for introducing the mobile phase, egress of the mobile phase, sparging and vacuum/vent access.

It will be understood that the details, dimensions, materials and arrangement of parts shown in the preferred embodiments have been described and illustrated to explain the nature of the invention. Changes may be made by those skilled in the art without departing from the principle and scope of the present invention as expressed in the appended claims.

What is claimed is:

1. A stopper or cap for a pressure chromatography column comprising a reservoir defining a chamber having means for maintaining a pressure above ambient pressure, said stopper or cap comprising:

(a) a body having an inlet adapted to communicate with the interior of a pressure chromatography column, an outlet downstream of said inlet, a seat interposed between said inlet and said outlet, said seat having an upstream side and a downstream side, said body also having a first bore extending downstream of said seat;

(b) a sealing element disposed downstream of said seat, said sealing element having an outer wall slidingly received in said first bore and a raised lip, said raised lip having an annular sealing surface enclosing a recess defining a piston surface, said raised lip being movable into and out of sealing relationship with said seat and having a smaller outer diameter than said outer wall, thereby defining an annular space between said first bore and said raised lip communicating with said outlet; and
(c) force applying means for urging said raised lip into sealing engagement with said seat.

2. A high performance liquid chromatography system comprising a mobile phase reservoir, said mobile phase reservoir having a chamber, means for maintaining a pressure above ambient pressure and a cap with a pressure-relief valve comprising:
(a) a body having an inlet, an outlet downstream of said inlet, a seat interposed between said inlet and said outlet, said seat having an upstream side and a downstream side, said body also having a first bore extending downstream of said seat;
(b) a sealing element disposed downstream of said seat, said sealing element having an outer wall slidingly received in said first bore and a raised lip, said raised lip having an annular sealing surface enclosing a recess defining a piston surface, relationship with said seat and having a smaller outer diameter than said outer wall, thereby defining an annular space between said first bore and said raised lip communicating with said outlet; and
(c) force applying means for urging said raised lip into sealing engagement with said seat.

3. A stopper or cap for a mobile phase reservoir for a high performance liquid chromatography system, said reservoir defining a chamber having means for maintaining a pressure above ambient pressure, said stopper or cap comprising:
(a) a body having an inlet adapted to communicate with the interior of a pressure vessel, an outlet downstream of said inlet, a seat interposed between said inlet and said outlet, said seat having an upstream side and a downstream side, said body also having a first bore extending downstream of said seat;
(b) a sealing element disposed downstream of said seat, said sealing element having an outer wall slidingly received in said first bore and a raised lip, said raised lip having an annular sealing surface enclosing a recess defining a piston surface, said raised lip being movable into and out of sealing relationship with said seat and having a smaller outer diameter than said outer wall, thereby defining an annular space between said first bore and said raised lip communicating with said outlet; and
(c) force applying means for urging said raised lip into sealing engagement with said seat. P

* * * * *